United States Patent
Gatti et al.

(10) Patent No.: US 8,241,237 B2
(45) Date of Patent: Aug. 14, 2012

(54) SYSTEM FOR MONITORING THE PRESSURE IN A BLOOD LINE AND A DEVICE TO BE USED IN SUCH A SYSTEM

(75) Inventors: Emanuele Gatti, Bad Homburg (DE); Jörg Jonas, Wehrheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1532 days.

(21) Appl. No.: 11/446,499

(22) Filed: Jun. 5, 2006

(65) Prior Publication Data

US 2006/0282036 A1   Dec. 14, 2006

(30) Foreign Application Priority Data

Jun. 3, 2005  (EP) .................................. 05011997

(51) Int. Cl.
- A61M 37/00 (2006.01)
- A61M 1/00 (2006.01)
- A61M 31/00 (2006.01)
- G01L 7/00 (2006.01)

(52) U.S. Cl. .............. 604/4.01; 604/27; 604/48; 73/706

(58) Field of Classification Search ................. 604/4.01, 604/27, 48; 422/44; 600/301, 310; 73/1.57, 73/19.05, 31.04, 438, 299, 700, 732, 738
See application file for complete search history.

(56) References Cited

U.S. PATENT DOCUMENTS

| | | | |
|---|---|---|---|
| 3,770,020 A * | 11/1973 | Tamura et al. ................ 137/802 |
| 4,267,040 A | 5/1981 | Schäl | |
| 4,493,693 A | 1/1985 | Bilstad et al. | |
| 4,834,108 A * | 5/1989 | Vaillancourt ................. 600/486 |
| 5,423,206 A * | 6/1995 | Hetzel ........................... 73/61.77 |
| 5,603,792 A * | 2/1997 | Guala et al. ................... 156/245 |
| 5,914,033 A * | 6/1999 | Carlsson ......................... 210/90 |
| 6,086,762 A * | 7/2000 | Guala ............................ 210/232 |
| 6,568,241 B2 * | 5/2003 | Cole ............................... 73/1.57 |
| 6,685,665 B2 * | 2/2004 | Booth et al. ...................... 604/26 |
| 2003/0130570 A1* | 7/2003 | Krivitski et al. .............. 600/322 |
| 2003/0154794 A1* | 8/2003 | Textor ............................. 73/706 |
| 2004/0237785 A1 | 12/2004 | Neri | |
| 2004/0254469 A1* | 12/2004 | Shkarlet et al. ............... 600/459 |
| 2005/0132826 A1* | 6/2005 | Teugels .......................... 73/866.5 |
| 2005/0230292 A1* | 10/2005 | Beden et al. .................... 210/85 |

FOREIGN PATENT DOCUMENTS

| EP | 1 547 630 | 6/2005 |
|---|---|---|
| JP | H10-505413 | 5/1998 |

* cited by examiner

Primary Examiner — Leslie Deak
Assistant Examiner — Adam Marcetich
(74) Attorney, Agent, or Firm — Jacobson Holman PLLC

(57) ABSTRACT

A system and device for monitoring pressure in a blood line. In such device, a pressure transducer line branches off a blood line to enable the connection of a pressure transducer. To avoid any contamination of the pressure transducer, a first pressure transducer protector filter is used that divides the pressure transducer line into a blood line section between the blood line and the filter, and a pressure transducer section between the filter and the pressure transducer. A sensor is provided for detecting the presence of liquid in the pressure transducer section of the pressure transducer line so as to provide a system by which an unnoticed failure of the first pressure transducer protector filter in a pressure transducer line is avoided as well as a device that can easily be re-used.

20 Claims, 2 Drawing Sheets

# SYSTEM FOR MONITORING THE PRESSURE IN A BLOOD LINE AND A DEVICE TO BE USED IN SUCH A SYSTEM

BACKGROUND OF THE INVENTION

1. Field of the Invention

The invention relates to the area of pressure monitoring devices for blood lines.

2. Description of the Related Art

In an extra-corporeal blood treatment blood is extracted from a patient, circulated in an extra-corporeal blood circuit that comprises a blood treatment unit, and infused back to the patient. Examples for such blood treatments are procedures to be used in case of kidney failure like hemodialysis, hemofiltration or hemodiafiltration. For other organ failures or diseases examples for blood treatments comprise blood oxygenation, blood component separation by centrifuge or filter techniques, or the removal of blood components by adsorption.

During the blood treatment blood is continuously or quasi-continuously circulated in the blood lines of the extra-corporeal blood circuit. In order to monitor the conditions in the extra-corporeal blood circuit the pressure in the arterial blood line leading from the patient to the blood treatment unit and in the venous blood line leading from the blood treatment unit to the patient are continuously measured. In contemporary devices this is accomplished by pressure transducer lines branching off the arterial and the venous lines, respectively, and leading to pressure transducers that are part of the blood treatment device.

To avoid any contamination of the pressure transducers and thus the blood treatment device a first pressure transducer protector filter is used that is dividing the pressure transducer line into a blood line section between the blood line and the filter and a pressure transducer section between the filter and the pressure transducer. Such a contamination is not desirable in view of a possible cross-contamination of the blood of a patient that is treated later with the same device. In addition, the spilled blood may damage the pressure sensor itself and the corresponding electronic circuits.

The pressure transducer protector filter is permeable by a gas like air but not by a liquid like blood. For this purpose preferably hydrophobic filter materials are used. Furthermore, the membrane element in the filter has pores small enough to block the transfer of matter like bacteria and germs that may compromise the sterile hygienic conditions in either side of the filter whenever air passes the filter.

The pressure transducer section is usually separable by connector means comprising a connector and a mating connector. It is thus possible to exchange and dispose the blood lines of the extra-corporeal circuit and the part of the pressure transducer line comprising the blood line section, the first pressure transducer protector filter and the pressure transducer section extending from the filter to the connector means after a blood treatment. These parts may be manufactured as a single piece blood line set. The remaining part of the pressure transducer line and the pressure transducer itself are part of the blood treatment device and are re-used for the next patient. As the first pressure transducer protector filter protects these parts from any blood contact there is no need to exchange them after proper use.

At the start of a treatment a new blood line set is mounted on the blood treatment device and the pressure transducer lines of the blood line set are connected with the help of the connector means to the blood treatment device. When the extra-corporeal blood circuit is primed with a priming solution before a patient is connected, a certain amount of air is trapped in the pressure transducer lines. The air nevertheless transmits the pressure from the corresponding blood line to the pressure transducer. When the pressure rises the air volume will be compressed, but the geometry of the lines is designed so that under normal conditions the blood level will not reach the first pressure transducer protector filter as otherwise the danger arises that the filter is blocked by the blood and that the pressure can no longer be properly transmitted though the filter.

As long as the integrity of the first filter is not damaged the blood cannot enter the pressure transducer section of the pressure transducer line and any contamination is avoided. As all parts of the blood line set that get into contact with the blood are replaced with new and sterile ones before the next patient is treated, cross-contamination cannot occur. The situation is however different should the first pressure transducer protector filter have a rupture. In this case blood can leak through the ruptured filter into the pressure transducer section. Contemporary hemodialysis devices therefore have a second pressure transducer protector filter in the pressure transducer section. The second filter is arranged inside the housing of the hemodialysis device and divides the pressure transducer section in a first part between the two filters and a second part between the second filter and the pressure transducer. This second filter is not part of the disposable blood line set and serves for redundancy purposes only. Should a blood leak occur in the first pressure transducer protector filter, the second pressure transducer protector filter still avoids any contamination and/or damage of the parts behind the second filter, in particular of the pressure transducer.

This prior art arrangement has the disadvantage that a rupture of the first filter is not necessarily noticed by the user of the blood treatment device. Any blood that passed the first filter may have contaminated any part of the first part of the pressure transducer section. In addition the membrane element of the second pressure transducer protector filter may have been at least partially blocked by the leaked blood. Though the pressure transducer is still protected by the second filter, this filter may no longer properly transmit the air pressure. Last not least, if not noticed by a user, the blood remaining in the first part of the pressure transducer section is not removed by exchanging the disposable blood line set, thus giving rise to a possible hygienic problem.

SUMMARY OF THE INVENTION

It is therefore an object of the present invention to provide a system by which an unnoticed failure of the first pressure transducer protector filter in a pressure transducer line is avoided. This problem is solved by a system for monitoring the pressure in a blood line, the system including a blood line, a pressure transducer line branching off the blood line and leading to a pressure transducer for measuring the pressure in the pressure transducer line, and a first pressure transducer protector filter in the pressure transducer line dividing the pressure transducer line into a blood line section between the blood line and the filter and a pressure transducer section between the filter and the pressure transducer. The first pressure transducer protector filter is permeable by a gas but not by a liquid. The system further includes a sensor for detecting the presence of a liquid in the pressure transducer section of the pressure transducer line.

Should the first pressure transducer protector filter have a rupture, leaking liquid will enter the pressure transducer section where the leaking liquid will be detected by the sensor that is arranged in this region of the pressure transducer line.

In a preferred embodiment of the invention the leaking liquid to be detected is blood or saline. Saline may be used as priming fluid for the blood line and as a kind of buffer between the blood in the blood line and the trapped air in the pressure transducer line to avoid any direct blood-air contact. In this case saline will primarily leak through the ruptured filter instead of blood. Any other liquid serving the same purpose may also be used. The selection of a sensor will depend on what leaking liquid is to be detected by the sensor.

In a specific embodiment of the invention, the sensor is an optical sensor for probing optical properties in the pressure transducer section, preferably the transparency of the pressure transducer section selectively at two light wavelengths.

In another embodiment of the invention the sensor is an electrical sensor for probing electrical properties in the pressure transducer section, in particular at least one of conductivity, capacity or inductance.

In a still further embodiment of the invention the sensor is an ultrasonic sensor including an ultrasonic transmitter and an ultrasonic transducer. With the aid of the ultrasonic sensor the transit times of ultrasonic signals through the pressure transducer section may be exploited to detect the presence of any liquid in this line.

In another embodiment of the invention the sensor is a first sensor for detecting a first liquid, with the system further including a second sensor for detecting the presence of a second liquid in the pressure transducer section of the pressure transducer line. The first sensor may be used to detect a first leaking liquid such as blood, and the second sensor to detect a second leaking fluid such as priming fluid, depending on the sensitivities of the sensors relative to the liquids to be detected. As an example, an optical sensor may be utilised for detecting the first fluid, e.g., blood, and an ultrasonic sensor may be used for detecting the second fluid, e.g., priming fluid. Two optical sensors using different optical wavelengths are a further example.

Depending on the coupling of the sensor or the sensors to the pressure transducer section, either conventional tubing systems or particularly shaped probe chambers like cuvettes may be used.

In a still further embodiment of the invention the system further includes a second pressure transducer filter dividing the pressure transducer section into a first part between the filters and a second part between the second filter and the pressure transducer. The second pressure transducer protector filter is also permeable by the gas but not by the liquid, and the sensor detects the presence of the liquid in the first part of the pressure transducer section.

The pressure transducer and the second pressure transducer protector filter may be fastened to a housing. The first part of the pressure transducer section may be separable by a connector including a first connector part and a second mating connector part, dividing the pressure transducer section into a housing section leading to the second pressure transducer protector filter and into a disposable section leading to the first pressure transducer protector filter, with the sensor detecting the presence of the liquid in the housing section of the first part of the pressure transducer section.

It is also an object of the invention to provide a device to be used in a system as described above by which an unnoticed failure of the first pressure transducer protector filter in the pressure transducer line is avoided and wherein the device itself can easily be re-used. This problem is solved by a device having the housing part of the embodiment of the system according to the invention where the system includes a disposable part and a housing part. The housing part includes the mating connector part, the second pressure transducer protector filter, the sensor for detecting the presence of the liquid in the pressure transducer section, the housing section of the first part of the pressure transducer section between the mating connector part and the second pressure transducer protector filter, the second part of the pressure transducer section and the pressure transducer. By joining the first connector part of the corresponding disposable part of the system according to the invention with the mating connector part of such a device, it is possible to detect any liquid leaking through a rupture in the first pressure transducer protector filter. In addition, the device can easily be re-used by disconnecting the disposable part with the help of the connector from the device. The disposable part can safely be discarded after use and be replaced by a new disposable part, e.g. blood line set, before the next treatment.

In a particularly advantageous embodiment of the invention, the device is a blood treatment device with a control unit for controlling and monitoring a blood treatment of blood that is circulated in an extra-corporeal blood circuit. In this case the extra-corporeal blood circuit further includes one or more blood lines having pressure transducer lines branching off the blood lines by which the pressure in the blood lines is determined by the control unit of the blood treatment device with the aid of the pressure transducers. For the treatment itself, the extra-corporeal blood is circulated through a blood treatment unit. Examples of such devices are hemodialysis, hemofiltration or hemodiafiltration devices where the blood treatment unit is a hemodialyser and/or hemofilter.

In a further embodiment of the invention the sensor for detecting the presence of a liquid is connected with the control unit of the blood treatment device such that the sensor emits a first signal to the control unit if no fluid is detected and a second signal to the control unit if the fluid is detected. The control unit may emit an alarm signal in case the second signal is received from the sensor.

The advantages of the present invention will become more apparent from an embodiment of the invention that is described as an example with the aid of the figures.

DETAILED DESCRIPTION OF THE PREFERRED EMBODIMENTS

Figure 1:
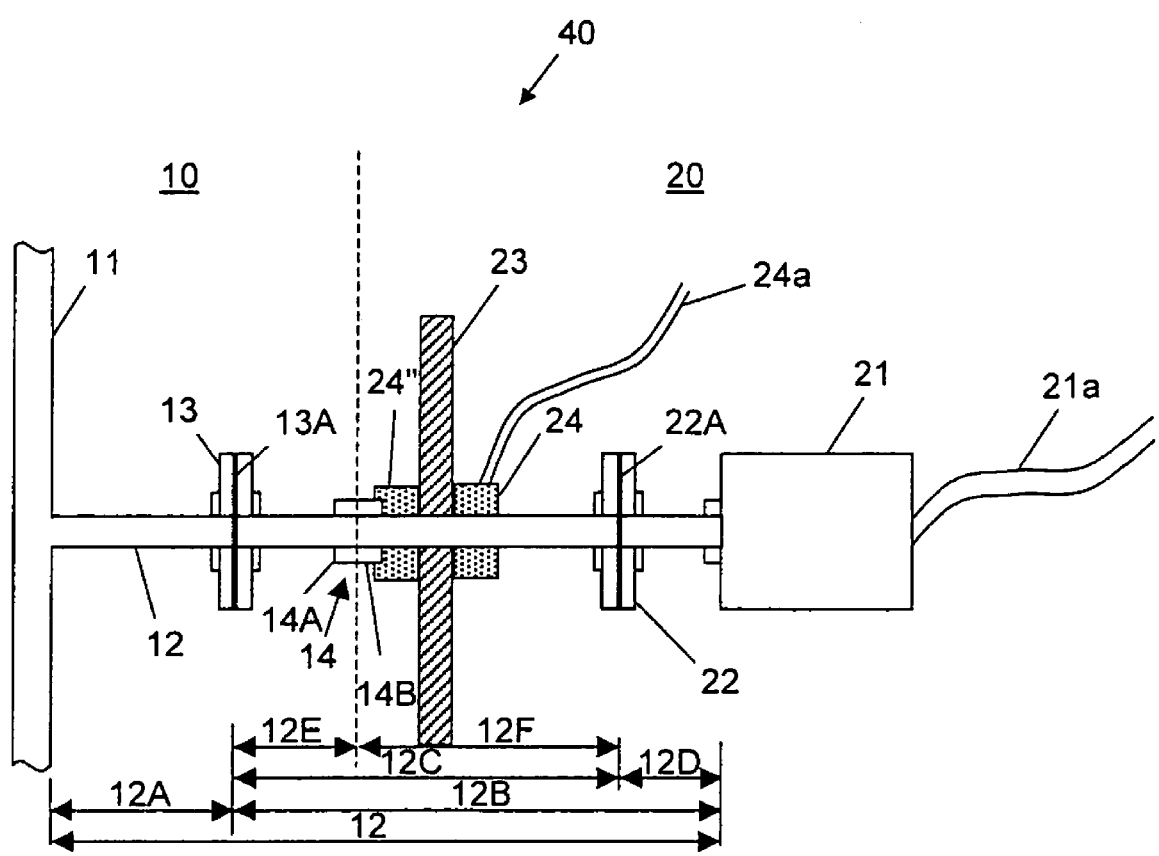
FIG. 1 illustrates an embodiment of a system according to the present invention including a reusable device and a disposable part.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

In FIG. 1, an example embodiment of a system generally designated by reference numeral 40 according to the present invention is shown. The system 40 includes a disposable part 10 being part of a disposable blood line set that can be exchanged after each use, and a reusable device 20 whose parts are not exchanged after each use. The disposable part 10 includes a blood line 11 from which the blood line section 12A of a pressure transducer line 12 branches off. The lines may be designed as a conventional tubing set. As an alternative, the lines may also be made as any kind of fluid guiding channels, in particular, as a part of a cartridge having rigid and/or flexible components. The pressure transducer line may branch off a blood tube directly or be accomplished as a part of a component, like an air trap, that is passed by the blood. In fact it is only necessary that the pressure transducer line 12 be in fluid contact with the blood line 10 so that the pressure can be transmitted though the pressure transducer line 12.

The pressure transducer line 12 is divided by a first pressure transducer protector filter 13 into a blood line section 12A between the blood line 11 and the first filter 13, and a pressure transducer section 12B between the first filter 13 and a pressure transducer 21. With the aid of the pressure transducer 21, the pressure in the pressure transducer line 12 and thus the blood line 11 is measured. As an example, the transducer may contain a piezoelectric element that converts the force and thus the pressure applied to it into an electrical signal as is well known in the art.

The pressure transducer section 12B is further divided by a second pressure transducer protector filter 22 into a first part 12C between the two filters, and a second part 12D between the second filter 22 and the pressure transducer 21 as shown in FIG. 1. The first part 12C is divided by a connector 14 into a disposable section 12E and a housing section 12F. The connector 14 includes a disposable connector part 14A mating with a housing connector part 14B. Such connector parts may be standard Luer lock connectors. The first and second pressure transducer protector filters 13 and 22 include hydrophobic filter membrane elements 13A and 22A that are permeable by a gas, such as air, but not by a liquid, e.g., blood or saline.

The disposable section 12E extends from the first pressure transducer protector filter 13 to the disposable connector part 14A. The housing section 12F extends from the housing connector part 14B to the second pressure transducer protector filter 22. Such an arrangement allows for an easy exchange of the disposable part 10 in this embodiment of the system according to the invention by disconnecting the disposable connector part 14A from the housing connector part 14B and replacing a used disposable part 10 with a new and sterile part 10.

The reusable device 20 of the system 40 includes a housing 23 to which the housing section 12F, the second part 12D of the pressure transducer section 12B, the second pressure transducer protector filter 22 and the pressure transducer 21 with wire connections 21a are fastened. For this purpose it is not necessary to fix all such components to the housing 23 individually as long as the ensemble is sufficiently secured to such housing.

In the pressure transducer section 12B, a sensor 24 with wire connections 24a is positioned. This sensor is an optical sensor element measuring the transparency of the pressure transducer section 12B at two suitable optical wavelengths or at least two distinct light colours. The first wavelength is chosen as a reference, and the second as a wavelength that is specific for the presence of the liquid to be detected, e.g., blood. Such two-colour sensors are already used for sensing the presence of blood in other parts of a blood treatment device and are known to the person skilled in the art. As a common example, such a sensor may use a red LED and a green LED as colour selective light sources. The light sources are preferably powered at a selected frequency so that their signal components in the detector signals can easily be filtered from any disturbing scattered light signals by conventional techniques. As light detectors, any light sensitive devices like photo diodes or transistors may be employed.

Alternative sensor embodiments may probe other properties, in particular electrical properties, of the pressure transducer section 12B in order to detect the presence of the liquid. Electrodes may be attached from the exterior to the pressure transducer section 12B and an alternating current source may be applied to the electrodes to probe the conductivity or capacity of the arrangement. Depending on the liquid to be detected, measurements utilising inductance may also be possible.

Figure 2:
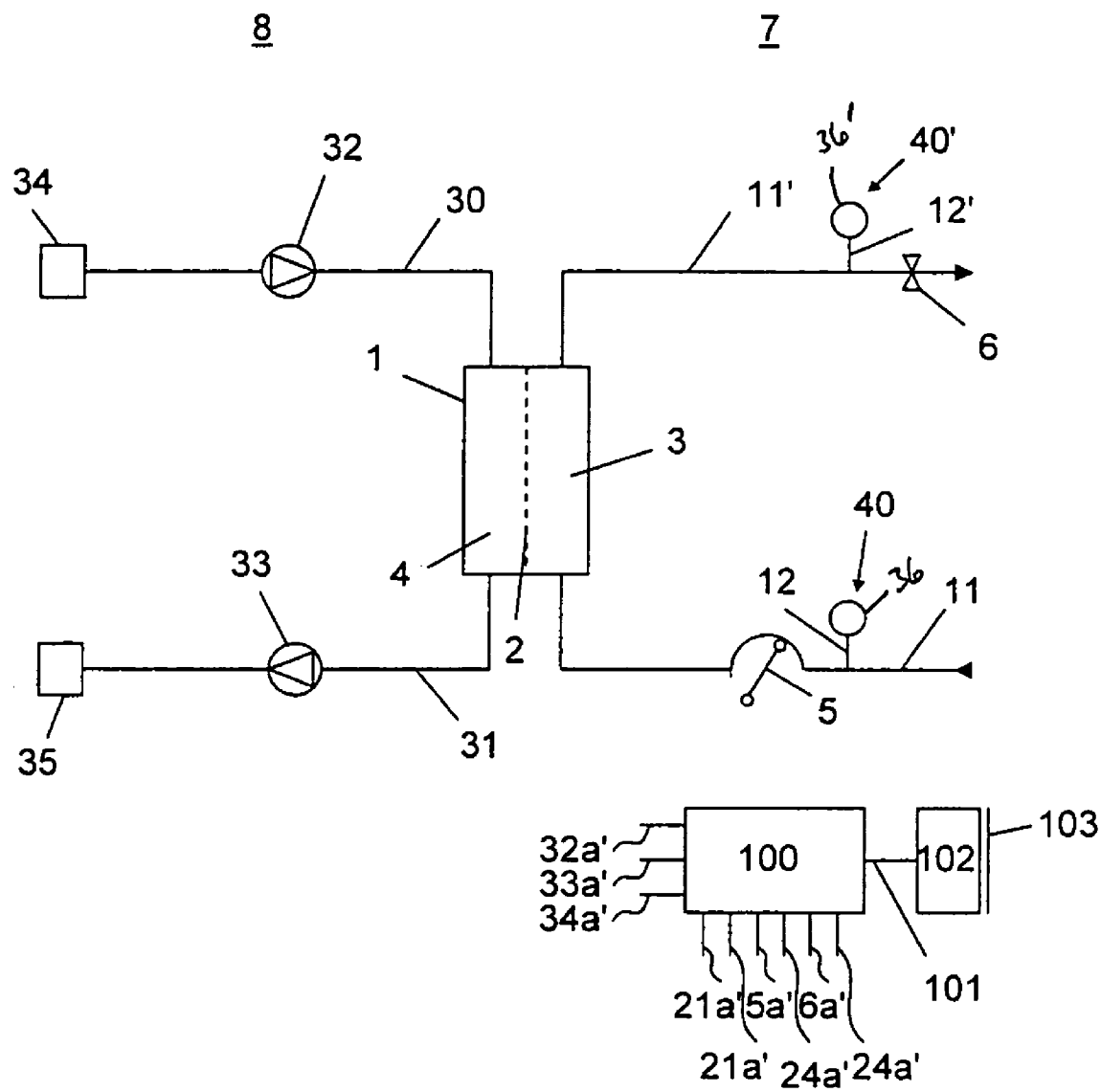
FIG. 2 shows a hemodialysis device with an extra-corporeal blood circuit having two systems of the type as depicted in FIG. 1.

If no blood is detected by the sensor 24, the sensor emits a first signal via the wire connections 24a to a control unit (see FIG. 2). Should blood enter the pressure transducer section 12B in case of a leak in the first pressure transducer protector filter 13, the optical properties of the pressure transducer section 12B will specifically change and the sensor 24 will emit a second signal to the control unit that is different from the first signal. The sensor 24 thus enables the system 40 to notify any user of the failure of the first pressure transducer protector filter 13.

In the embodiment as shown in FIG. 1, the sensor 24 is positioned between the housing 23 and the second pressure transducer protector filter 22, i.e. not on the side that is directly accessible by a user who usually has direct access to the connector 14 to replace the disposable part 10. In FIG. 1, an alternative arrangement is also shown where the sensor 24" is positioned between the housing 23 and the housing connector 14B. Depending on the individual device 20, one of the two alternatives may be preferable.

FIG. 2 shows a hemodialysis device with an extra-corporeal blood circuit including a first system 40 and a second identical system 40' as depicted in FIG. 1. In hemodialysis, blood of a patient (not shown) is circulated in an extra-corporeal blood circuit (not shown) from an arterial blood line 11 to a hemodialyser 1. The hemodialyser is separated by a semipermeable membrane 2 that is usually embodied by a bundle of hollow fibres in a first compartment 3 (blood compartment), that is part of the extra-corporeal blood circuit, and a second compartment 4 (dialysate compartment), that is part of a dialysate circuit (not shown). Substances to be removed by the blood treatment pass the membrane 2 from the blood compartment 3 to the dialysate compartment 4 and are removed by the dialysate that circulates though the dialysate compartment 4. At the same time, excess fluid in the blood can be removed from the blood by applying an appropriate pressure gradient across the membrane 2. A diffusion gradient can be used to transfer substances present in the fresh dialysate, like electrolytes, into or remove them from the blood to achieve a certain concentration level of these substances in the blood.

The blood is circulated by a blood pump 5 that may be a conventional roller pump. The blood enters the blood compartment 3 of the dialyser 1 via the arterial blood line 11 and leaves it via the venous blood line 11' by which the blood is re-infused into the patient (not shown). A venous clamp 6 is mounted on the venous blood line 11'. The venous clamp 6 can be closed whenever the re-infusion of the blood should be interrupted because of safety reasons. An example of such a safety reason is the detection of a certain amount of air in the venous blood 11' by an air sensor (not shown).

The second compartment 4 of the hemodialyser 1 is connected with a dialysate inlet line 30 by which dialysate fluid is guided from a dialysate preparation unit 34 to the second compartment 4. It is also connected with a dialysate outlet line 31 by which the dialysate is guided from the second compartment 4 to a drain 35. The dialysate is circulated by pumping and balancing means 32 and 33 by which the fluid rates in the dialysate inlet and outlet lines 30 and 31, and thus also the ultrafiltration rate by which fluid is extracted from the blood, can be accurately controlled. Embodiments for such pumping and balancing means 32 and 33 are well known in the art. The same applies for the dialysate preparation unit 34. An example embodiment for the pumping and balancing means 32 and 33 and the dialysate preparation unit 34 is described in U.S. Pat. No. 4,267,040.

Conventional hemodialysis devices contain many further components as is also well known in the art. For the purpose of simplicity, the description of FIG. 2 is limited to those components that appear to be sufficient for an understanding of the concept of the present invention.

The hemodialysis device is controlled and monitored by a control unit 100 which is connected with the various sensors and actuators of the device by signal connections. These connections may be wired or wireless. In FIG. 2, these connections are depicted schematically by using the same reference numbers for the connections and the connected sensors/actuators, with the suffix 'a' being added for the connections. For clarity, only those ends of the connections that terminate at the control unit 100 are shown in FIG. 2.

The control unit 100 is further connected with an input and output unit 102 by a data link 101. The input and output unit 102 may include a touchscreen 103 that can be used to display selected information that is provided by the control unit 100. At the same time, a user may enter further data and/or instructions into the control unit 100 by using the touchscreen 103.

The hemodialysis device as shown in FIG. 2 also includes a system 40 according to the invention as shown in detail in FIG. 1. From the arterial blood line 11 of the extra-corporeal blood circuit, a pressure transducer line 12 branches off that leads to an arterial pressure transducer 36. In FIG. 2 the system 40 is only depicted symbolically. The same applies for an identical system 40' that includes a pressure transducer line 12' branching off the venous blood line 11' and leading to a venous pressure transducer 36'.

The wire connections 21a and 24a as shown in FIG. 1 are connected with the control unit 100 as shown in FIG. 2. This applies to the connections 21a' and 24a' of the second system 40' also. Using these connections, the control unit 100 receives signals from the sensor 24 of the system 40 and the corresponding sensor 24' of the system 40'. The sensors emit a first signal to the control unit 100 if no blood is detected by the sensor, and a second signal if blood is detected. This terminology is not limited to a system and device where the sensor processes the measurement signal itself and, as a result, transmits only two kinds of signals in the sense of 'yes' or 'no'. The sensor may transmit signals that are partly pre-processed by the sensor electronic circuits, or not pre-processed at all. The first signal only has to be distinct from the second signal. Hence, the first signal may include a first range of signal values and the second signal a second range of signal values, with both ranges being separated by a threshold value. In case the signals are not pre-processed and the sensor produces pairs or multiples of signals, as in the case of an optical sensor that probes the transparency at two wavelengths, such a pair or multiple of signals will be directly processed by the control unit 100. Though the final transparency result is then calculated by the control unit, the transmission of such pair or multiple signals to enable the derivation of a final result is considered to be encompassed by the wording that the sensor emits first and second signals dependent on the presence of the liquid in the pressure transducer section 12B.

In case at least one of the sensors 24 or 24' emits the second signal to the control unit 100, the control unit will send a corresponding signal to the input and output unit 102 so that an alarm signal will be displayed on the touchscreen 103 to make a user aware of a pressure transducer protector filter integrity problem in either of the pressure transducer lines. Preferably the user will be notified in which of the two pressure transducer lines the alarm condition was detected. Other alarm signals, like audible alarms and/or transmitting the alarm signal to remote locations by a communication network, may also be initiated by the control unit 100. As an optional further feedback, the control unit 100 may advise the venous clamp 6 to close the venous blood line 11' and the other pumps to stop or to switch into a special pause mode if required.

As the blood lines of the extra-corporeal blood circuit are usually disposed of after a blood treatment, the corresponding blood line set includes only the disposable blood set part 10 of the systems 40 and 40', respectively. The hemodialysis device itself, without the blood lines, only has to contain the components of the reusable device 20 of the systems 40 and 40' as outlined above in the context of the description of FIG. 1. In this case the housing 23 is preferably the housing of the hemodialysis device. On the outside of the housing the housing connector part 14B is mounted by which a user can connect the disposable connector part 14A of the blood line set. The other components of the reusable device 20 are preferably contained inside the housing 23 or at least as shown in FIG. 1. The user only has to access these components in case of a faulty part, as in the case when blood has been sensed by the sensor 24. It may then be necessary to replace the housing section 12F of the pressure transducer line 12 and the second pressure transducer protector filter 22. The housing 23 of the hemodialysis device may then be opened as for technical maintenance or some other suitable way to allow access to the components.

With the aid of the sensor 24, the control unit 100 may check the integrity of the system at any time before, during or after a blood treatment. In particular, during the priming process a check of the integrity by probing the presence of the priming fluid can avoid any otherwise necessary trouble shooting during the blood treatment in case the checks are only taking place during the blood treatment. Regular checks should be performed to ensure that the sensor is correctly working wherein conventional fail safe techniques may be applied. Should a problem be detected just after a blood treatment, this is also helpful as an early exchange of the necessary parts is enabled.

The system and the device according to the present invention provide an easy and efficient way to avoid blood contamination problems and the non-detection of faulty pressure transducer protector filters particularly in blood treatment devices where the pressure in blood lines has to be routinely monitored at one or more locations. A higher hygienic standard can thus be achieved. The device according to the present invention may be integrated in a blood treatment device during the manufacturing process. Because few additional components are needed, it is also easily possible to use the device according to the present invention in older blood treatment devices by installing appropriate retrofit kits. Such kits only require a software update for the control unit of the blood treatment device and the additional sensor for detecting the presence of liquid in the pressure transducer section of the pressure transducer line.

The invention may be used for any line carrying blood or any components of blood to be processed by a blood treatment device. It is not limited to the processing of whole blood.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed:

1. A system for monitoring the pressure in a blood line comprising:
   a bloodline;
   a pressure transducer line branching off the blood line and leading to a pressure transducer for measuring the pressure in the pressure transducer line;
   a first pressure transducer protector filter in the pressure transducer line dividing the pressure transducer line into a blood line section between the blood line and the first filter, and a pressure transducer section between the first filter and the pressure transducer, the first pressure transducer protector filter being permeable by a gas but not by a liquid,
   a first sensor configured to detect the presence of a first liquid in the pressure transducer section of the pressure transducer line; and
   a second sensor configured to detect the presence of a second liquid in the pressure transducer section of the pressure transducer line, said second liquid being different than said first liquid and
   said second sensor for detecting said second liquid being of a different type or configured differently than said first sensor.

2. The system according to claim 1, wherein the first liquid is blood and the first sensor is configured to detect blood and the second liquid is saline and the second sensor is configured to detect saline.

3. The system according to claim 1, wherein at least one of the first sensor and the second sensor is an optical sensor configured to probe optical properties in the pressure transducer section.

4. The system according to claim 3, wherein the at least one sensor is configured to measure a transparency of the pressure transducer section selectively at two light wavelengths or at least selectively for two light colors.

5. The system according to claim 1, wherein at least one of the first sensor and the second sensor is an electrical sensor configured to probe electrical properties in the pressure transducer section.

6. The system according to claim 5, wherein the electrical properties are at least one of conductivity, capacity or inductance.

7. The system according to claim 1, wherein at least one of the first sensor and the second sensor is an ultrasonic sensor including an ultrasonic transmitter and an ultrasonic transducer.

8. The system according to claim 1, wherein the system further comprises a second pressure transducer protector filter dividing the pressure transducer section into a first part between the first and second filters and a second part between the second filter and the pressure transducer, said second pressure transducer protector filter also being permeable by gas but not by a liquid, and said first sensor configured to detect the presence of the first liquid in the first part of the pressure transducer section.

9. The system according to claim 8, wherein the first part can be separated and joined by a connector having a first connector part and a second connector part.

10. The system according to claim 9, wherein the system is divided by the connector into a disposable part and a housing part, the disposable part including the blood line, the blood line section, the first pressure transducer protector filter, the first connector part and a disposable section of the first part of the pressure transducer section between the first pressure transducer protector filter and the first connector part, and the housing part including the second connector part, the second pressure transducer protector filter, the first sensor, the second sensor, a housing section of the first part of the pressure transducer section between the second connector part and the second pressure transducer protector filter, the second part of the pressure transducer section and the pressure transducer.

11. The system according to claim 10, wherein the housing part further includes a housing to which the other components of the housing part are fastened.

12. The system according to claim 11, wherein at least one of first and second sensors is positioned between the housing and the second pressure transducer protector filter.

13. The system according to claim 11, wherein at least one of first and second sensors is positioned between the housing and the second connector part.

14. The system according to claim 1 wherein the first liquid is blood and the first sensor is an optical sensor configured to detect blood and the second liquid is priming fluid and the second sensor is an ultrasonic sensor configured to detect priming fluid.

15. A device to be used in a system for monitoring pressure in a blood line that includes a bloodline, a pressure transducer line branching off the blood line and leading to a pressure transducer for measuring the pressure in the pressure transducer line, and a first pressure transducer protector filter in the pressure transducer line dividing the pressure transducer line into a blood line section between the blood line and the first filter, and a pressure transducer section between the first filter and the pressure transducer, the first pressure transducer protector filter being permeable by a gas but not by a liquid, said device comprising:
   a second pressure transducer protector filter dividing the pressure transducer section into a first part between the first and second filters and a second part between the second filter and the pressure transducer, said second pressure transducer protector filter also being permeable by gas but not by a liquid;
   a first sensor configured to detect the presence of a first liquid in the first part of the pressure transducer section; and
   a second sensor configured to detect the presence of a second liquid in the first part of the pressure transducer section, said second liquid being different than said first liquid and
   said second sensor for detecting said second liquid being of a different type or configured differently than said first sensor.

16. The device according to claim 15 wherein the device is a blood treatment device and further includes a control unit for controlling and monitoring a blood treatment of blood circulating in an extra-corporeal blood circuit in which the blood line is a part of the extra-corporeal blood circuit.

17. The device according to claim 16 wherein the device is a hemodialysis, hemofiltration of hemodiafiltration device.

18. The device according to claim 16 wherein the first sensor is connected with the control unit and the first sensor emits a first signal to the control unit if the first liquid is not detected and a second signal to the control unit if the first liquid is detected.

19. The device according to claim 18 wherein the control unit emits an alarm signal upon receipt of the second signal.

20. The device according to claim 15 wherein the first liquid is blood and the first sensor is an optical sensor configured to detect blood and the second liquid is priming fluid and the second sensor is an ultrasonic sensor configured to detect priming fluid.

* * * * *